United States Patent [19]

Schildgen et al.

[11] Patent Number: 5,853,652

[45] Date of Patent: Dec. 29, 1998

[54] METHOD OF MANUFACTURING A MEDICAL ELECTRICAL LEAD

[75] Inventors: Gary R. Schildgen, White Bear Lake; Charles R. Wait, Minneapolis, both of Minn.

[73] Assignee: Medtronic, Inc., Minneapolis, Minn.

[21] Appl. No.: 632,429

[22] PCT Filed: Oct. 14, 1994

[86] PCT No.: PCT/US94/11651

§ 371 Date: Apr. 24, 1996

§ 102(e) Date: Apr. 24, 1996

[87] PCT Pub. No.: WO95/11723

PCT Pub. Date: May 4, 1995

Related U.S. Application Data

[63] Continuation-in-part of Ser. No. 146,265, Oct. 29, 1993, abandoned.

[51] Int. Cl.⁶ .................................. B28B 1/24; B22F 7/00
[52] U.S. Cl. .......................... 264/614; 264/102; 264/618; 264/642; 419/2; 419/8
[58] Field of Search ............................... 264/60, 61, 104, 264/125, 614, 618, 642, 645, 669, 101, 102; 419/2, 8

[56] References Cited

U.S. PATENT DOCUMENTS

| | | | |
|---|---|---|---|
| 2,129,240 | 12/1938 | Sanborn | 25/45 |
| 2,513,785 | 4/1950 | Browne | 18/55 |
| 3,929,476 | 12/1975 | Kirby, Jr. et al. | 75/214 |
| 4,113,480 | 9/1978 | Rivers | 75/214 |
| 4,149,542 | 4/1979 | Thoren | 128/418 |
| 4,414,028 | 11/1983 | Inoue | 419/31 |
| 4,431,449 | 2/1984 | Dillon et al. | 75/246 |
| 4,502,492 | 3/1985 | Bornzin | 128/785 |
| 4,506,680 | 3/1985 | Stokes | 128/786 |
| 4,556,096 | 12/1985 | Nagata et al. | 164/79 |
| 4,577,642 | 3/1986 | Stokes | 128/784 |
| 4,582,682 | 4/1986 | Betz et al. | 419/68 |
| 4,603,704 | 8/1986 | Mund et al. | 128/784 |
| 4,606,118 | 8/1986 | Cannon et al. | 29/825 |
| 4,612,160 | 9/1986 | Donlevy et al. | 419/2 |
| 4,677,989 | 7/1987 | Robblee | 128/784 |
| 4,711,251 | 12/1987 | Stokes | 128/784 |
| 4,773,433 | 9/1988 | Richter et al. | 128/784 |
| 4,784,160 | 11/1988 | Szilagyi | 128/784 |
| 4,784,161 | 11/1988 | Skalsky et al. | 128/785 |
| 4,819,661 | 4/1989 | Heil, Jr. et al. | 128/786 |
| 4,819,662 | 4/1989 | Heil, Jr. et al. | 128/786 |
| 4,927,600 | 5/1990 | Miyashita et al. | 419/49 |
| 4,929,415 | 5/1990 | Okazaki | 419/52 |
| 4,936,317 | 6/1990 | MacGregor | 128/784 |
| 4,936,909 | 6/1990 | Takeshima et al. | 75/364 |
| 5,080,672 | 1/1992 | Bellis | 623/16 |
| 5,094,985 | 3/1992 | Kijima et al. | 501/88 |
| 5,097,843 | 3/1992 | Soukup et al. | 128/784 |
| 5,106,709 | 4/1992 | Tekkanat et al. | 429/210 |
| 5,122,043 | 6/1992 | Matthews | 425/77 |
| 5,147,722 | 9/1992 | Koslow | 428/402 |

OTHER PUBLICATIONS

Bernard Williams, "Current Status of Injection Moulding of Metal Powders and Ceramics", Metal Power Report, vol. 41, 1986, pp. 359–364.

B. Haworth, P.J. James, "Injection Moulding of Powders", Metal Power Report, vol. 41, 1986, pp. 46–149.

*Primary Examiner*—Christopher A. Fiorilla
*Attorney, Agent, or Firm*—Michael J Jaro; Harold Patton

[57] ABSTRACT

A method of manufacturing a lead having an electrode includes the steps of introducing a substrate into a mold, creating a negative pressure in the mold, injecting a slurry comprising a binder and a conductive particulate material into the mold cavity during the step of creating negative pressure in the mold cavity, heating the mold having the substrate and the particulate material in an oven to cojoin the particulates and thereby form an electrode, removing the mold from the oven, removing the electrode from the mold, and assembling the electrode into a lead. The produced lead may be used as a steroid eluting pacing cardiac lead.

21 Claims, 5 Drawing Sheets

METHOD OF MANUFACTURING A MEDICAL ELECTRICAL LEAD

REFERENCE TO RELATED APPLICATIONS

This is a continuation-in-part of application Ser. No. 08/146,265 entitled "MEDICAL ELECTRICAL LEAD AND METHOD OF MANUFACTURE" of Gary R. Schildgen filed Oct. 29, 1993 now abandoned.

BACKGROUND OF THE INVENTION

1. Field of the Invention

This invention relates generally to medical electrical leads and methods of manufacture thereof and, in particular, to a method of manufacturing a sintered porous platinized electrode used in a steroid eluting pacing cardiac lead which produces an electrode having increased dimensional consistency over previously used manufacturing methods.

2. Description of the Prior Art

The safety, efficacy and longevity of an implanted pacemaker system depends, in part, on the performance of the pacing leads, the electronic circuits and the integrity of the pulse generator, and the capacity and reliability of the pulse generator power source. These inter-related components of an implanted pacemaker system optimally are matched in a fashion that accommodates ever increasing demands on the modes of operation and function of the system in conjunction with an overall reduction in system size, an increase in system longevity and an increased expectation in system reliability.

During the past thirty years, the technology of cardiac pacing has significantly advanced. Implantable pacing systems offer an ever increasing variety of pacing modalities, thereby substantially broadening the indications for pacemaker use. In conjunction with this advancement, there has been extensive research and development to optimize the performance of pacing leads and their reliability while concurrently simplifying their manufacture.

In the past ten years, substantial improvements in chronic pacemaker sensing and stimulation thresholds have been achieved which, in turn, have allowed the development of smaller and longer-lived pacemakers that can be used with smaller leads. As new circuits are developed with lower "overhead" current drains, however, and as the circuits increase in complexity to allow for ever increasing pacemaker capabilities in their programmable functions, modes and memory, pacemaker longevity depends increasingly more on the characteristics of the lead. In addition, many doctors prefer pacing leads be made ever thinner, to occupy less space in the venous system, without diminishing or detracting from the mechanical strength and integrity of the lead body.

Recently, various investigators have emphasized materials and their relationship to the considerations involved in optimizing electrode design. For example, Bornzin, U.S. Pat. No. 4,502,492 owned by Medtronic, Inc. discloses a low polarization, low threshold electrode design which was commercialized as the TARGET TIP® lead during the early to mid-1980's. That design featured a generally hemispherical electrode with circular grooves, fabricated from platinum and coated over its external surface with a plating of platinum black. This combination of the relatively low (8 mm$^2$) macroscopic electrode surface area and relatively high microscopic electrode surface area (due to the use of platinum black) contributed to the achievement of state-of-the-art thresholds for that time period. Other manufacturers marketed electrodes of other materials and configurations including totally porous platinum mesh (Cardiac Pacemakers, Inc.), porous surface sintered (Cordis Corporation), glassy and vitreous carbons (Siemens Inc.), and laser drilled metal (Telectronics Ltd.) electrodes in that same time period.

A considerable breakthrough in the development of low threshold electrode technology occurred with the invention of the steroid eluting porous pacing electrode of Stokes, U.S. Pat. No. 4,506,680 and related Medtronic U.S. Pat. Nos. 4,577,642; 4,606,118 and 4,711,251, all incorporated herein by reference. The electrode disclosed in the Stokes '680 patent was constructed of porous, sintered platinum or titanium, although carbon and ceramic compositions were also mentioned. Proximate the electrode a plug of silicone rubber impregnated with the sodium salt of dexamethasone phosphate, or a water soluble form of other glucocorticosteroids, was placed. The silicone rubber plug allowed the release of the steroid through the interstitial gaps in the porous sintered metal electrode to reach the electrode-tissue interface and prevent or reduce inflammation, irritability and subsequent excessive fibrosis of the tissue adjacent to the electrode itself. The porous steroid eluting electrode presented a sensing impedance substantially lower compared to similarly sized solid electrodes and presented significantly lower peak and chronic pacing thresholds than similarly sized solid or porous electrodes. The advantages of the steroid eluting electrode allowed a relatively small surface area electrode of about 5.5 mm$^2$ (CAPSURE® SP Model 5023, 5523 leads sold by Medtronic, Inc.) to raise lead impedance without sacrificing the ability to sense heart activity.

The smaller electrode size was important because it resulted in higher current density during stimulation pulses. This, in turn, was important because it provided more efficient stimulation of the heart tissue with lower current drain from the implanted pacemaker power source. This resulted in overall increased longevity of the implanted pacemaker system.

Lead impedance is a function of the resistance of the lead conductor and the stimulating electrode as well as the effective impedance of the electrode-tissue interface. An inefficient way to raise impedance is to increase the resistance of the lead conductor. This wastes current as heat. It is preferable to decrease lead current drain with more efficient control of the stimulating electrode-tissue interface impedance. This can be done by reducing the geometric surface area of the electrode.

Recent advances in lead design have continued decreasing the exposed geometric surface area of the electrode. One such example is disclosed in Stokes et al. U.S. patent application Ser. No. 07/887,560 filed May 18, 1992 entitled "High Impedance, Low Polarization, Low Threshold Miniature Steroid Eluting Pacing Lead Electrodes" now U.S. Pat. No. 5,282,844 incorporated herein by reference, which discloses a lead featuring a porous platinized steroid eluting electrode exhibiting an effective surface area in the range of 0.1 to 4.0 mm$^2$, and preferably between 0.6 to 3.0 mm$^2$ which offers increased pacing impedance without increasing thresholds and without negatively impacting sensing capabilities over previously lead, and in particular, electrode designs. The particular lead disclosed in the before-mentioned application offers a pacing impedance of at least 1400±260 ohms, and a source impedance of at least 1650±410 ohms. Such a lead, however, due to its size requires an electrode which is relatively more difficult to consistently manufacture, especially with respect to electrode diameter and concentric dimension.

Previously, porous platinized steroid eluting electrodes were sometimes manufactured using a slurry-drip process. Specifically a slurry mixture of platinum particles and a liquid organic binding agent was created. To form the electrode, a substrate, typically a straight shank of wire, had the slurry mixture dripped onto one end of the substrate. A portion of the slurry mixture stuck to the substrate. After several applications of the slurry mixture (between 10 to 50 separate applications) an acceptable mass of the mixture is built up on the end of the substrate. The substrate is then sintered to drive off the binder and conjoin or fuse the platinum particles together. This manufacturing process generally yields an electrode having acceptable electrical characteristics.

With the ever smaller size of cardiac leads, however, dimensional variance of the electrode has a relatively greater impact. In particular the slurry-drip method of electrode manufacture has been found to not offer the dimensional consistency desired in present-day relatively smaller leads. Because leads are smaller than ever before, the same dimensional variance in electrode size now has a relatively larger effect upon lead quality than it did when leads were relatively larger. Specifically, under conditions of mass production the resultant electrode is many times dimensionally inconsistent, e.g. eccentric, too large or too small and thus unacceptable. Such inconsistency increases the number of rejected leads, and thus results in higher manufacturing costs. In addition dimensional inconsistency may impair electrical performance, possibly impairing performance of the pacing system.

SUMMARY OF THE INVENTION

It is thus an object of the present invention to provide a medical electrical lead and method of manufacture, and specifically an electrode used in such a lead, which has increased dimensional consistency over previously provided leads and methods of manufacture.

The present invention concerns a medical electrical lead, and in particular to a method of manufacturing a sintered porous platinized electrode used in a steroid eluting pacing cardiac lead which offers increased dimensional consistency over previously used manufacturing methods. The method of manufacturing the electrode of the present invention permits the electrode to be more consistently manufactured with respect to its dimensions and desired shape characteristics. The method of the present invention also permits such an electrode to be constructed using a substrate tailored to achieve the desired impedance. For example in one embodiment of the present invention an electrode is constructed with a nailhead-shaped substrate which provides for a higher impedance lead to be constructed. The method of manufacturing the electrode portion of a medical electrical lead of the present invention basically comprises the steps of mixing a conductive material and a binder to form a slurry; providing an electrode substrate within a mold; creating a negative pressure in the mold; injecting the slurry into the mold; releasing the negative pressure in the mold; sintering the mold, conductive material and substrate, to drive off the binder and harden or conjoin the conductive material together.

BRIEF DESCRIPTION OF THE DRAWINGS

These and other objects and advantages of the present invention may be fully understood and appreciated in conjunction with the attached drawings and the following detailed description of the preferred embodiment where the same numerals are employed to denote the same or similar features throughout.

The drawings are not necessarily to scale.

DETAILED DESCRIPTION OF THE DRAWINGS

As a general comment, the present invention preferably includes the use of a steroid or other drug with the electrode. The electrode may be configured to allow the drug to be eluted through and/or around the electrode in order to reach the endocardial or myocardial cells near the distal end of the pacing lead in order to reduce, if not eliminate entirely, the inflammation and irritation caused by the presence of a lead and especially in response to the tip of a lead. As described in Stokes, U.S. Pat. No. 4,506,680 and related Medtronic U.S. Pat. Nos. 4,577,642; 4,606,118 and 4,711,251, mentioned above, the electrode is preferably fabricated from a body compatible electrically conductive material with or without specific steroid eluting passages but generally with a porous structure either throughout the body of the electrode or at its surface. The porosity of the electrode surface or body provides a large surface area for sensing whereas the overall dimension or shape of the exposed electrode defines a comparatively smaller surface area for stimulation. The porous structure thus presents a relatively large microscopic (or "fractal") surface area for sensing and a relatively very small macroscopic or geometric surface area for stimulation. Acceptable electrode materials and the associated fabrication techniques employed to achieve the micro-porous structure, as well as the porosity of that structure are all set forth in the aforementioned prior art patents and in the Richter et al., U.S. Pat. No. 4,773,433; Heil Jr. et al., U.S. Pat. No. 4,819,661; Thoren et al., U.S. Pat. No. 4,149,542; Robblee, U.S. Pat. No. 4,677,989; Heil Jr. et al., U.S. Pat. No. 4,819,662; Mund et al., U.S. Pat. No. 4,603,704; Skalsky et al., U.S. Pat. No. 4,784,161; Szilagyi, U.S. Pat. No. 4,784,160, herein incorporated by reference.

The present invention concerns an electrode used in a medical electrical lead, and in particular to a method of manufacturing an electrode used in a sintered porous platinized electrode used in a steroid eluting pacing cardiac lead which offers increased dimensional and shape consistency over previously used manufacturing methods. The method of the present invention also permits such an electrode to be constructed using a substrate tailored to achieve the desired impedance. For example in one embodiment of the present invention an electrode is constructed with a nailhead-shaped substrate which provides for a higher impedance lead to be constructed.

Lead

Figure 1:
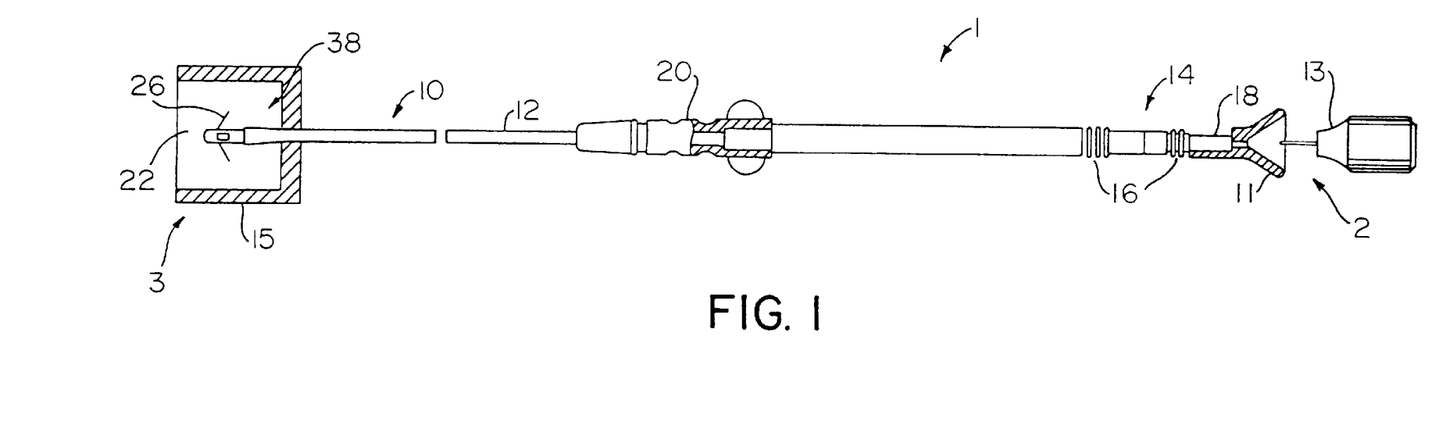
FIG. 1 is a plan view of an endocardial, unipolar pacing lead according to the present invention.

FIG. 1 illustrates a plan view of an endocardial, unipolar lead constructed in accordance with the present invention.

The lead 1 includes an elongated lead body 10 covered by an insulative sleeve 12. Insulative sleeve 12 may be fabricated of any flexible biocompatible and biostable insulator especially silicone rubber or polyurethane. At the proximal end 2 of lead 1, terminal assembly 14 is adapted to couple lead 1 to an implantable pacemaker pulse generator (not shown.) Terminal assembly 14 is provided with sealing rings 16 and a terminal pin 18, all of a type known in the art. An anchoring sleeve 20 (shown partially in cross-section) slides over lead body 10 and serves as a point for suturing lead body 10 to body tissue at the insertion point of lead 1 in a fashion known in the art. Anchoring sleeve 20 and terminal assembly 14 are preferably fabricated of silicone rubber, although they may also be constructed of any other suitable biocompatible material known in the art.

Lead 1, as shown in FIG. 1, further includes a stylet guide 11 and stylet assembly 13 coupled to terminal pin 18 for imparting stiffness to lead 1 during the insertion and placement of lead 1 transvenously into either the right ventricle or the right atrium of the heart (not shown.) Stylet guide 11 and stylet assembly 13 are discarded after use and before connection of terminal pin 18 to a pacemaker pulse generator (not shown.)

At distal end 3 of lead 1, a tine protector 15 is shown (in cross-section) protecting tine assembly 38 having a series of tines 26 until lead 1 is used. Tines 26 are employed to passively retain electrode 22 in position against the endocardium (not shown) as is well known in the pacing art.

Figure 2:
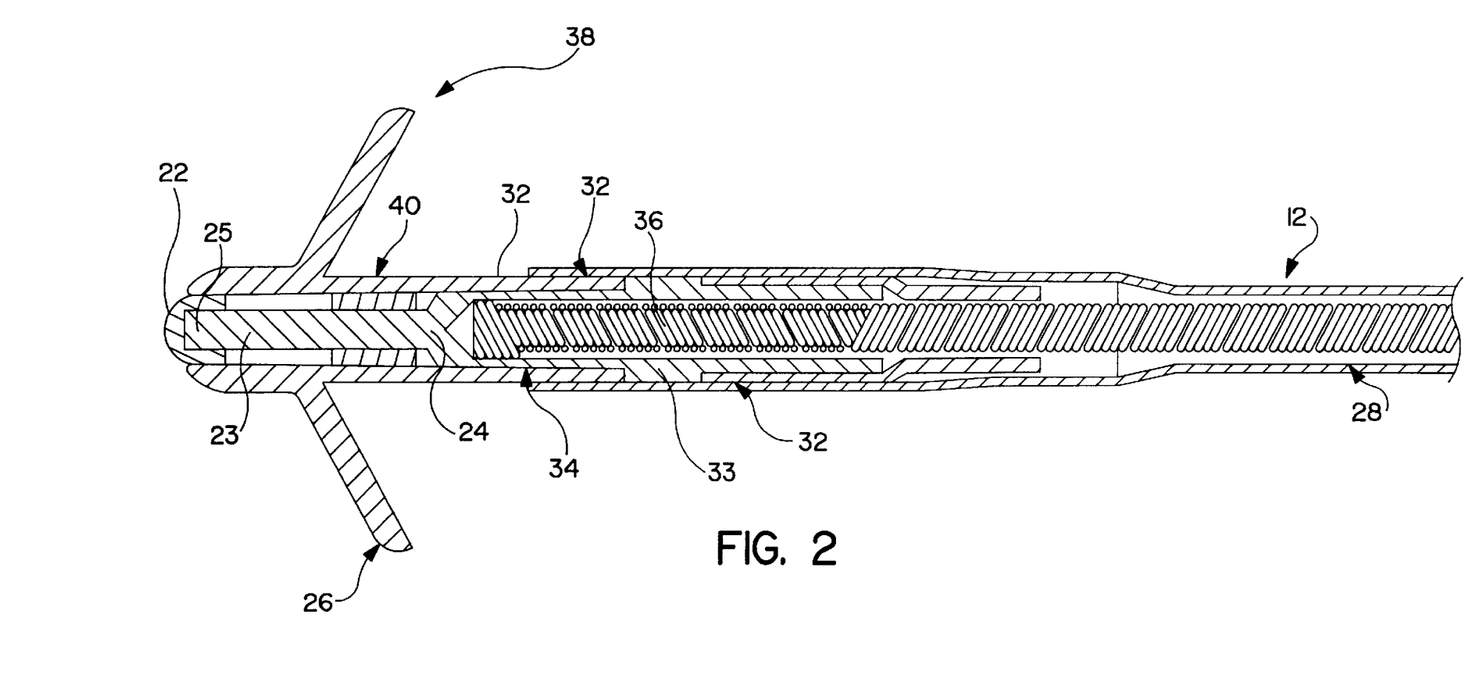
FIG. 2 shows a cross-sectional view of the distal end of the lead shown in FIG. 1.
Figure 5:
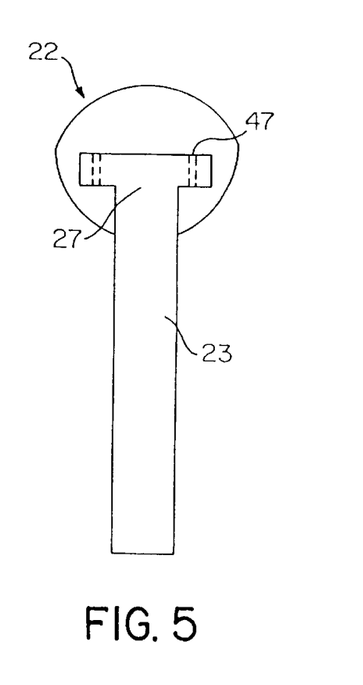
FIG. 5 shows an electrode constructed according to the present invention for use in a medical electrical lead and featuring a nail-head shaped substrate.

FIG. 2 shows in cross-section proximal end and distal end of lead 1 of the present invention. As seen lead 1 includes conductor coil 28 extending throughout, i.e., from terminal pin 18 to electrode 22. Preferably conductor coil 28 is multifilar in construction. Substrate 23 is depicted as a substantially straight piece of a conductive material, such as a platinum alloy, although substrate may be formed into other shapes, such as having a nail-head shaped distal end 27, as best seen in FIG. 5. A substrate having a nail-head shaped distal end 27 has been found to offer a somewhat higher impedance electrode than those featuring a straight shank substrate. Nail-head shaped distal end 27 may be formed in any manner, such as through heat, including actually melting distal end 27 to the desired shape, mechanical deformation, or even molding substrate having such a distal end. Any shape, however, functioning to increase impedance to the electrode 22 and thus lead 1 may be used. In addition, the overall length of electrode 22 may be shortened and a series of holes 47 may be provided radially about raised surface 24, as best seen in FIG. 5, to provide for an increased elution rate of steroid from steroid-silicone compound ring 40 (discussed below) to the distal tip of electrode 22. Further discussion and disclosure regarding other shaped electrode substrates may be found in the United States patent application of Gates entitled "Substrate For A Sintered Electrode" filed Apr. 30, 1993 and incorporated herein by reference.

Electrode 22 is depicted as a porous platinum object covered with platinum black at the end of substrate 23. Although platinum is the preferred material for electrode 22 and substrate 23, they may additionally include or be made entirely from various other materials, including but not limited to such materials as palladium, titanium, tantalum, rhodium, iridium, carbon, vitreous carbon and alloys, oxides and nitrides of such metals or other conductive materials. Of course, some materials are incompatible with others, such as a platinum substrate with a titanium electrode, and may not be effectively used together. The limitations of specific materials for use with others is well known in the art.

Moreover, although in the preferred embodiment electrode 22 is manufactured from a spherical platinum powder, other forms of conductive particulate materials besides spherical may be used, including such forms as fines, fibers or polyhedrons.

Substrate 23 extends from electrode 22 to distal end of conductor coil 28 where it is attached to proximal end 24 of substrate 23 by crimping at point 34 of crimping member 36 at the time of manufacture. An adhesive, such as a silicone medical adhesive, may be used at various points 32 to seal against leakage of fluid, such as blood, into conductor coil 28. Insulative sleeve 12 is placed over skirt 33 and crimping member 36 as well as proximate tine assembly 38. Steroid-silicone compound ring 40 is located proximate to electrode 22.

Steroid-silicone compound ring 40 forms a monolithic controlled release device when it is loaded with an anti-inflammatory agent, e.g., a steroid dexamethasone sodium phosphate. The steroid also is deposited within the pores of electrode 22 by application of a solution of 200 mg U.S.P. dexamethasone sodium phosphate dissolved in 5.0 cc isopropanol and 5.0 cc distilled or deionized water as described in the aforementioned Stokes' patents. Weight and composition of steroid-silicone compound ring 40 as well as the electrode surface area are critical to the overall performance of electrode 22. In particular steroid-silicone compound ring 40 is positioned proximate said electrode to dispense a drug in the vicinity of body tissue.

In a preferred embodiment electrode 22 has a macroscopic surface area of less than 4.0 mm$^2$ exposed to the body tissue or fluids or both and more preferably, but not limited to, in the range of 0.10 and 4.0 mm$^2$. The surface of electrode 22 exposed to the body tissue or fluids or both is generally hemispherical. The small geometric macroscopic electrode size is intended to produce very high pacing impedance. The porous surface configuration together with platinum black electroplating and steroid contribute to a microscopically large surface area for low polarization, low source impedance and low thresholds. The porous surface also facilitates the retention of steroid and adhesion of the platinum black to the electrode surface. The electrode 22, therefore, permits steroid to elute therethrough. The electrode 22 and lead, especially tine assembly 38, may preferably be dimensioned, moreover, to further allow steroid to elute around the electrode 22, i.e., between electrode 22 and tine assembly 38.

Mold

Figure 3:
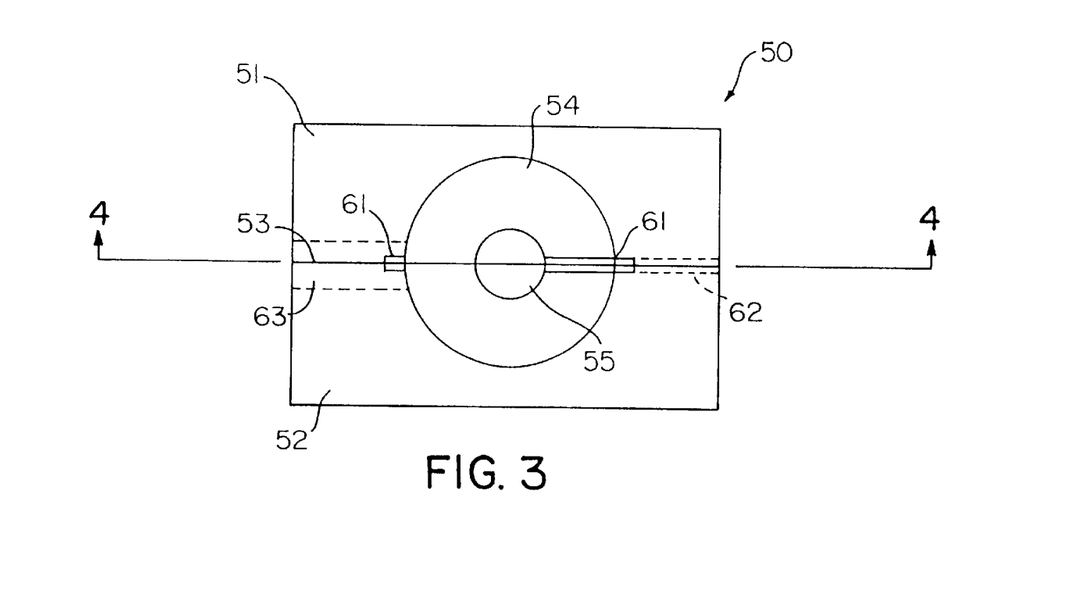
FIG. 3 shows a cross-sectional view of a mold used to form an electrode used in a lead of the present invention.

Mold 50 is constructed from two identical halves 51, 52 separable along mold-line 53, as seen in FIG. 3. Preferably mold 50 is constructed from a rigid material having a high melting point so as to permit mold 50 to withstand the heat if electrode 50 is sintered in an oven. In the preferred embodiment mold 50 is constructed from an isotropic material having a high melting point, such as ultrafine graphite, although other materials may be used, such as carbide. In a preferred embodiment the ultrafine graphite used for mold 50 has an average particle size of 5 microns or less. Other material which could also be used would be heat resistant carbide or carbide alloys having principal alloying elements of nickel or chromium. Such a carbide mold may additionally be provided with a coating, such as graphite, tungsten, titanium or vanadium.

Figure 4:
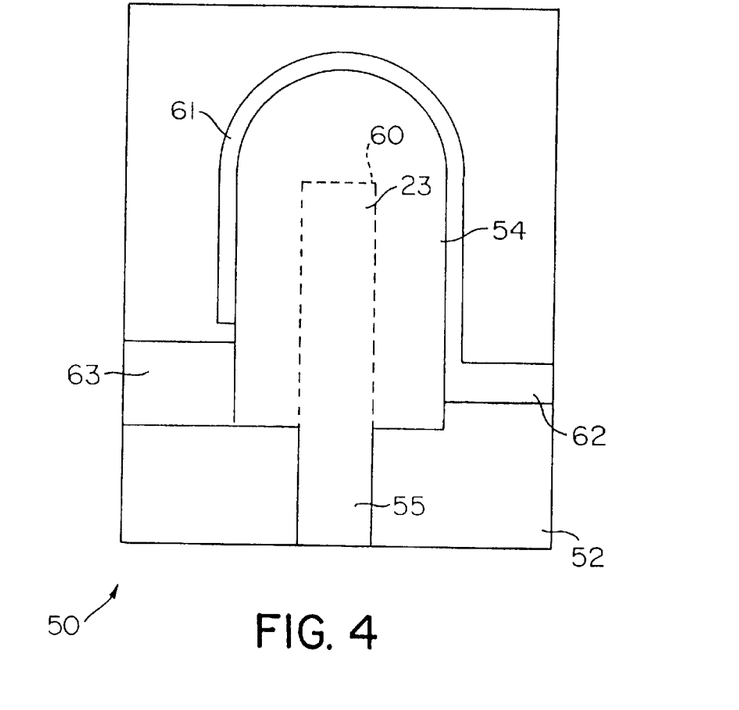
FIG. 4 shows a cross-sectional view of the mold shown in FIG. 3 taken along the line 3—3.

Provided within mold 50 is mold cavity 54 which conforms to the desired shape of electrode 22. Substrate port 55 permits substrate 23 to be inserted into mold cavity 54, as seen in FIG. 4 in phantom outline 60, and permits the conductive material to be applied thereon.

Suction groove 61 connects with suction port 62 to permit a negative pressure, such as a vacuum, to be created in mold cavity 54. Suction groove 61 is dimensioned so as to have a width of less than the width of whatever conductive material is used. For example in a preferred embodiment of a lead, an electrode constructed from a spherical platinum powder having an average particle diameter from 0.000984 to 0.001260 inches (25–32 microns) would be used with a suction groove 61 having a width of 0.0008 inches (20.3 microns.) In such a manner a negative pressure using suction groove 61 would not permit conductive particulate material to flow within and clog suction port 62.

Mold cavity 54 is also constructed having injection port 63 opening within. Injection port 63 thereby permits a conductive material to be injected into mold cavity while a negative pressure, such as a vacuum, is created therein through suction port 62 and suction groove 61. Through the concurrent creation of a negative pressure while the conductive material is injected into the mold cavity 54 a complete fill of mold cavity 54 is accomplished, which, in turn, because mold is rigid, ensures a properly shaped and dimensioned electrode to be manufactured.

Method of Manufacture

As discussed above, electrode 22 is manufactured by a process of injecting a mixture into mold cavity while, preferably, concurrently creating a negative pressure, such as a vacuum, with mold cavity 54.

Figure 8:
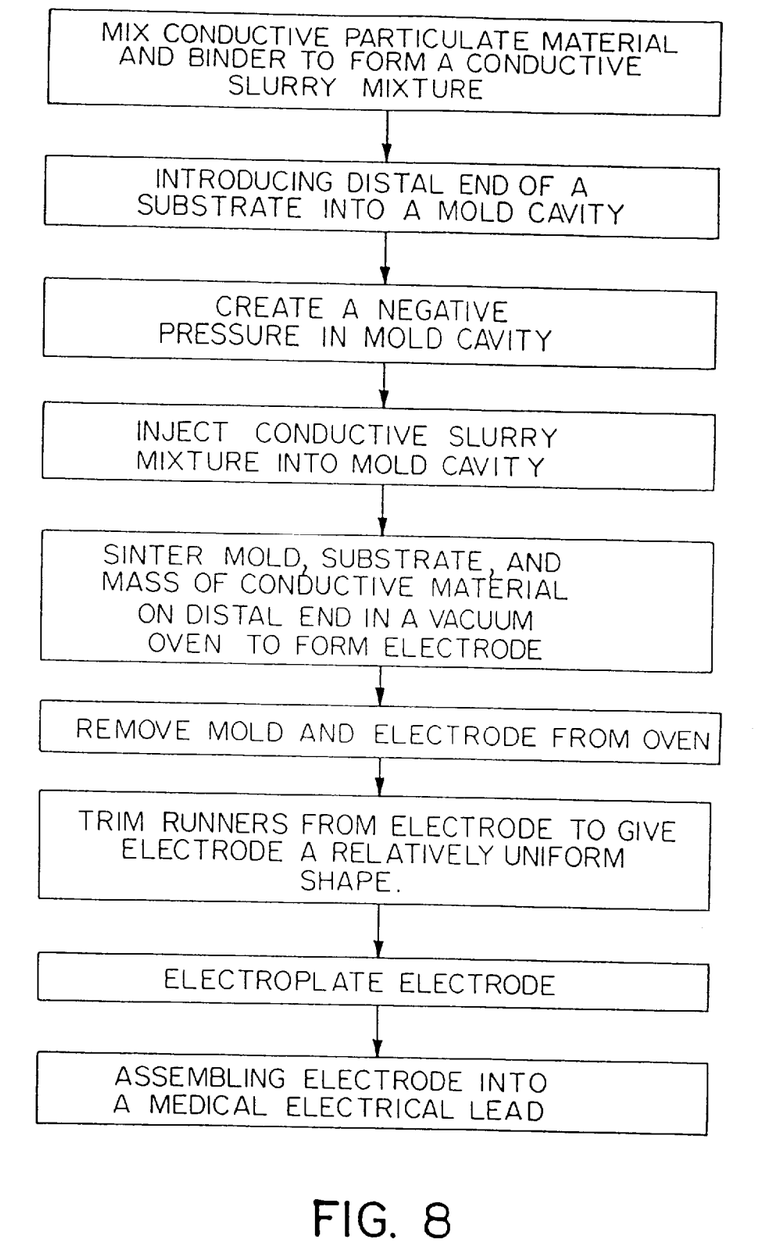
FIG. 8 illustrates the method of manufacturing a medical electrical lead according to the present invention.

The first step of the manufacturing process, as seen in FIG. 8, comprises mixing a conductive particulate material and a binder to form a conductive slurry mixture. In a preferred embodiment, conductive mixture comprises 70 weight percent of a spherical platinum powder and 30 weight percent of a binder solution. The preferred binder solution consists of 2 percent of an organic binder, such as KLUCEL™ manufactured by Aqualon Corp. of Wilmington, Del. and 98 percent deionized water. The relative proportions of these constituents has been found to influence the ultimate porosity of the electrode produced. Specifically, the greater the amount of binder to conductive particulate material, the relatively higher porosity electrode produced.

The next step comprises introducing distal end 25 of substrate 23 into a mold 50, and specifically into mold cavity 54 as depicted by phantom line 60 of FIG. 4.

Next, a negative pressure, such as a vacuum, is created in mold cavity 54 through suction port 62 and suction groove 61. Then, while under negative pressure, the conductive mixture is injected into mold cavity 54 so as to substantially fill mold cavity 54 and form a mass of conductive material on distal end 25 of substrate 23. In the preferred embodiment a negative pressure of between 20 to 27 inches of mercury is used. The amount of pressure used, however, depends, in part, upon the desired porosity of the electrode to be formed.

Once formed, the mixture and substrate are sintered, as is well known in the art, to draw off the binder and harden or conjoin the conductive particulate material together as well as to substrate 23. In a preferred embodiment, sintering is accomplished by placing the entire assembly, viz. mold 50 having substrate 23 therein and mass of conductive particulate material on distal end 25 into a vacuum oven at 2475 degrees fahrenheit for one hour. Sintering may further be accomplished through any other methods suited to harden the conductive material to substrate 23 while removing binder, such as electrical sintering.

Next, the mold 50 is removed from the sintering device, an oven in the preferred embodiment of the present invention, and electrode 22 is removed from mold 50. Any runner formed through solidification of mixture material within injection port is then removed to give electrode a relatively uniform shape.

Electrode 22 is then preferably electroplated with a material to provide a relatively high microscopic surface area, such as platinum black in the preferred embodiment. Electroplating may be accomplished in any manner suitable. In the preferred embodiment, electroplating of electrode 22 with a platinum black material is accomplished as follows. First, to assure good adhesion of the platinum black electrode 22 is cleaned. After suitably cleaning, electrode 22 may be platinized by immersing electrode 22, as cathode, in a platinizing solution, such as one consisting of three percent (3%) platinum chloride dissolved in 0.025 percent lead acetate solution. An anode of inert metal may then be placed into the platinizing solution and a sufficient current passed through the cell so that small bubbles are visible at the electrode 22. This process should be continued until a layer of platinum black is deposited over the entire electrode. This process, cleaning and platinizing, produces an electrode having a platinum black surface coating which is sufficiently durable to permit it to be implanted within a body. The porosity of electrode 22, together with the platinum black coating is intended to reduce source impedance and polarization, as is well known in the art.

The final step comprises providing or assembling electrode 22 into a medical electrical lead 1, such as one shown in FIG. 1. This step may comprise the steps of providing an electrical conductor having a first end and a second end, an insulating sleeve covering the electrical conductor between the first end and the second end, coupling a connector to the first end of the electrical conductor, and coupling the electrode to the second end of the electrical conductor for conducting electrical energy to and from a body.

Figure 6:
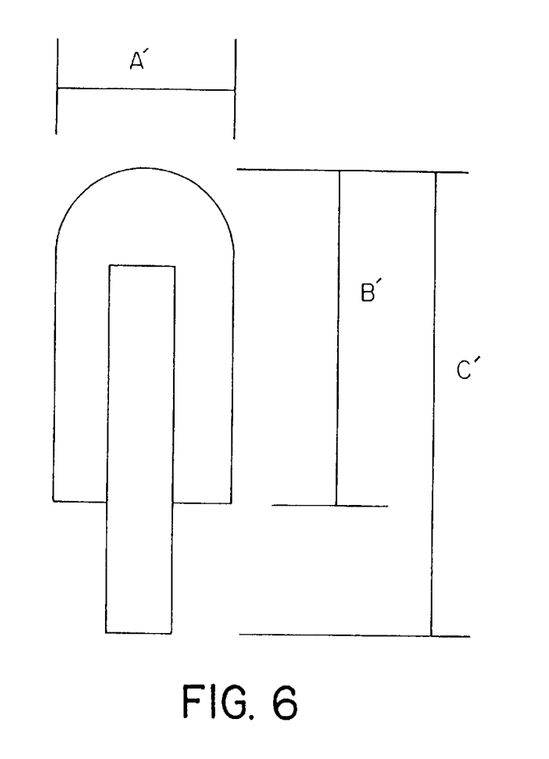
FIGS. 6 and 7 illustrate the various dimensions of an electrode constructed according to the present invention.
Figure 7:
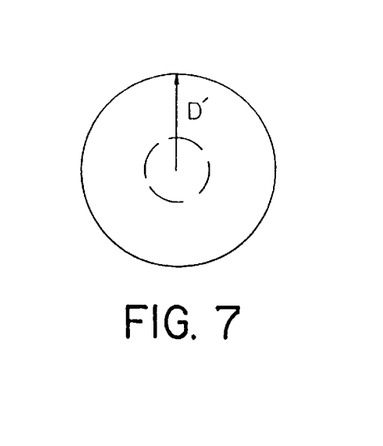

FIGS. 6 and 7 show various dimensions A'–D' of an electrode constructed according to the present invention. Shown below is a comparison of measurements and the standard deviations (in parentheses) for electrodes made using the prior art slurry-drip process and the process of the present invention.

| Electrode | METHOD USED | |
| --- | --- | --- |
| Dimension | Slurry-Drip | Present-Invention |
| A' | 0.0374 (0.0015) | 0.0366 (0.0002) |
| B' | 0.0370 (0.002) | 0.0360 (0.001) |
| C' | 0.053 (0.010) | 0.247 (0.0025)* |
| D' | 0.001 (0.003) | 0.001 (0.0001) |

*Note: difference size produced.

Thus it is seen that relatively small electrodes may be more consistently constructed and manufactured according to the present invention which satisfy the aforementioned desirable characteristics of a pacing lead, i.e. low stimulation thresholds, relatively low polarization, good to excellent sensing, and adequately low source impedance. Higher pacing impedance prolongs the longevity of pacing pulse generators and allows for the miniaturization of their components.

While the embodiments of the present invention have been described in particular application to cardiac pacing, and in particular to endocardial pacing leads it will be understood the invention may be practiced in other electrode technologies where the aforementioned characteristics are desirable, including epicardial leads as well as neurological and muscle stimulation applications.

Moreover, although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. A method of manufacturing a lead (1) having an electrode (22) used to stimulate and sense a body comprising the steps of introducing a substrate (23) into a mold (50) having a mold cavity (54) and positioning a conductive particulate material onto the substrate (23) in the mold cavity (54), the step of positioning a conductive particulate material onto the substrate (23) characterized in that:

creating a negative pressure in the mold cavity (54) through a first port (62) in the mold (50);

injecting a slurry comprising a binder and a conductive particulate material into the mold cavity (54) during the step of creating the negative pressure in the mold cavity (54);

heating the mold (50) having the substrate (23) and the particulate material in an oven to conjoin the particulates and thereby form an electrode (22);

removing the mold (50) from the oven;

removing the electrode (22) from the mold (50), and assembling the electrode into a lead.

2. The method of manufacturing according to claim 1 further comprising the step of creating a negative pressure in the oven during the sintering.

3. The method of manufacturing according to claim 2 wherein the negative pressure in the oven is a vacuum.

4. The method of manufacturing according to claim 1 further comprising the step of forming a raised surface on a distal end (27) of the substrate (23).

5. The method of claim 4 wherein the forming the raised surface on a distal end (27) of a substrate (23) comprises deforming with heat the distal end of the substrate (23).

6. The method of claim 5 wherein the deforming with heat comprises melting the distal end (27) of the substrate (23).

7. The method of claim 4 wherein the forming the raised surface on the distal end (27) of the substrate (23) comprises mechanically deforming the distal end of the substrate (23).

8. The method of claim 1 wherein the conductive particulate material is selected from the group of platinum, palladium, titanium, tantalum, rhodium, iridium, carbon, and alloys, and oxides or nitrides of such metals.

9. The method of claim 8 wherein the conductive particulate material is spherical.

10. The method according to claim 8 wherein the conductive particulate material is fines.

11. The method of manufacturing according to claim 1 further comprising the steps of:

providing an electrical conductor (28) having a first end and a second end, an insulating sleeve (12) covering the electrical conductor (28) between the first end and the second end;

coupling a connector (14) to the first end of the electrical conductor (28); and coupling the electrode (22) to the second end of the electrical conductor (28) to thereby form a lead used for conducting electrical energy to and from a body.

12. The method according to claim 11 further comprising positioning a drug dispenser (40) proximate the electrode (22).

13. The method according to claim 12 wherein the step of positioning a drug dispenser (40) proximate the electrode (22) further comprises positioning a drug dispenser having an anti-inflammatory agent.

14. The method according to claim 13 wherein the step of positioning a drug dispenser (40) proximate the electrode (22) further comprises positioning a drug dispenser having a salt of dexamethasone phosphate.

15. The method according to claim 12 wherein the drug dispenser (40) comprises a water permeable polymer body located within the insulating sleeve (12) and adjacent the electrode (22) containing a water soluble form of the drug.

16. The method according to claim 1 wherein the electrode (22) formed is porous.

17. The method of claim 1 wherein the mold (50) is graphite.

18. The method of claim 1 wherein the mold (50) is carbide.

19. The method according to claim 1 further comprising the step of coating a surface of the electrode (22) with platinum black.

20. The method according to claim 1 wherein the step of injecting a conductive particulate material into the mold cavity (54) further comprises mixing a conductive particulate material and a binder and injecting the mixture of the conductive particulate material and the binder in the mold cavity (54) through a second port (63).

21. The method of claim 1 wherein the mold (50) is anisotropic material.

* * * * *